(12) United States Patent
Reid et al.

(10) Patent No.: US 7,932,440 B2
(45) Date of Patent: Apr. 26, 2011

(54) COTTON VARIETY

(75) Inventors: Peter Ewan Reid, Narrabri (AU); Gregory Arthur Constable, Narrabri (AU); Warwick Nigel Stiller, Narrabri (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 803 days.

(21) Appl. No.: 11/222,712

(22) Filed: Sep. 8, 2005

(65) Prior Publication Data

US 2007/0056062 A1 Mar. 8, 2007

(51) Int. Cl.
*A01H 5/00* (2006.01)
*A01H 5/10* (2006.01)
*A01H 4/00* (2006.01)
*A01H 1/00* (2006.01)
*C12N 15/82* (2006.01)

(52) U.S. Cl. ........ 800/314; 800/260; 800/278; 800/300; 435/410

(58) Field of Classification Search .................. 800/260, 800/278, 295, 300, 314; 435/410, 421, 430
See application file for complete search history.

(56) References Cited

U.S. PATENT DOCUMENTS

| 1,725,268 | A | * | 8/1929 | Hancock | 19/59 |
| 5,869,720 | A | * | 2/1999 | John | 800/314 |
| 6,008,438 | A | * | 12/1999 | Keim | 800/314 |
| 7,053,281 | B2 | * | 5/2006 | Robinson et al. | 800/314 |

OTHER PUBLICATIONS

Poehlman, J.M. and D.A. Sleper. 1995. Breeding Field Crops. 4th ed. Iowa State University Press, Ames, Iowa, p. 473.*
Hansen et al, Trends in Plant Science 4(6): 226-231, 1999.*
Zhao et al, Molecular Breeding 8:323-333, 2001.*
Dow AgroSciences, Risk assessment and risk management plant, DIR 040/2003, Nov. 2003, p. 25, paragraph 115.*
CSIRO Plant IndustryPlant Varieties Journal, vol. 13, No. 3, 2002, pp. 9, 24 and Figure 33.*
Delta Farm Press. EPA clears Bollgard II for 2003 use, Jan. 10, 2003.*
Fehr. 1987. Backcross method. In Principles of cultivar development, vol. 1, Theory and technique. p. 362.*
Mills et al (Agronomy Journal 100(1): 35-41, 2008).*

* cited by examiner

*Primary Examiner* — Medina A. Ibrahim
*Assistant Examiner* — Keith O. Robinson
(74) *Attorney, Agent, or Firm* — John P. White; Cooper & Dunham LLP

(57) ABSTRACT

The present invention relates to a new cotton (*Gossypium hirsutum*) variety, and more particularly to cotton plants and cotton seeds of this new variety. The invention also relates to F1 hybrid cotton plants and seeds produced using the new variety, as well as to transgenic cotton plants and seeds produced by transformation of this new variety.

21 Claims, No Drawings

COTTON VARIETY

FIELD OF THE INVENTION

The present invention relates to a new cotton (*Gossypium hirsutum*) variety, and more particularly to cotton plants and cotton seeds of this new variety. The invention also relates to F1 hybrid cotton plants and seeds produced using the new variety, as well as to transgenic cotton plants and seeds produced by transformation of this new variety.

BACKGROUND OF THE INVENTION

Cotton is an important and valuable field crop which is used to manufacture textile products, oil, animal feed, cordage and other non-woven products. Cotton production today is based mainly on cultivation of varieties of the species *Gossypium hirsutum*, known as Upland cotton. These cotton varieties are generally preferred for their high lint yield potential, early maturity, and adaptation to adverse climatic and growing conditions. On the other hand, the quality of Upland cotton lint is considered low to medium.

Varieties of another species, *G. barbadense*, known as Pima cotton, constitute only 5-8% of the world cultivated cotton area. Pima varieties typically produce superior lint having long, strong and fine fibre. On the other hand, these varieties usually have low yield potential, require a long growing season, and can only be cultivated in warm regions.

Cotton lint quality is measured by a number of measures including fibre length, strength and micronaire. Accordingly, the lint quality is considered higher when the fibre is longer, stronger and finer when the fibre is fully matured in open boll. The present invention provides a new *G. hirsutum* variety producing lint having long fibre length, as well as good strength and mid-range micronaire.

SUMMARY OF THE INVENTION

According to one aspect of this invention, there is provided a plant of the cotton (*Gossypium hirsutum*) variety Sicala 350B, or a part, cell, tissue or organ thereof.

Embodiments of this aspect of the present invention also relate to seed of the cotton plant; a tissue culture of regenerable cells of the cotton plant; a tissue culture regenerating plants capable of expressing all the morphological and physiological characteristics of the cotton plant; and a tissue culture regenerated from cells or protoplasts of a tissue selected from the group consisting of seeds, leaves, stems, pollens, roots, root tips, anthers, ovules, petals, flowers, embryos, fibres and bolls.

The present invention also relates to a cotton plant produced by growing the seed as described above, or regenerated from a tissue culture as described above, or a part, cell, tissue or organ of such a plant.

According to another aspect of the present invention there is provided a method for producing an F1 hybrid cotton plant using plant breeding techniques which employ the cotton plant as described above, or a part, cell, tissue or organ thereof, as a source of plant breeding material. The method of this aspect of the invention further relates to plant breeding techniques selected from the group consisting of recurrent selection, backcrossing, pedigree breeding, restriction fragment length polymorphism enhanced selection, genetic marker enhanced selection, and transformation.

In related aspects, the present invention provides for methods of producing F1 hybrid cotton seed and further, F1 hybrid cotton seed which comprise a gene that confers herbicide tolerance to plants. Accordingly, further provided are hybrid cotton plants which comprise a gene that convers herbicide tolerance to plants.

In yet another aspect, the invention provides a method for producing a transgenic cotton plant by transformation of a cotton plant as described above, or a part, cell, tissue or organ thereof.

Definitions

As used herein, the terms "lint yield" or "yield" refer to the measure of the quantity of fibre produced, after ginning, on a given unit of land, for example bales/hectare (b/ha) or preferably kilograms/hectare (kg/ha).

As used herein, lint % (also known as "gin turnout") refers to the weight of the lint after ginning as a percentage of the weight of the seed cotton.

As used herein, the terms "fibre length" or "length" refer to the 2.5% span length in inches (or 32nds=$\frac{1}{32}$ inch) of fibre as measured by High Volume Instrumentation (HVI). Such instrumentation and methods for use are standard and well known in the industry.

As used herein, the terms "fibre strength" or "strength" refer to the force required to break a bundle of fibres as measured in grams/tex on the HVI.

As used herein, the term "micronaire" refer to the fibre periphery at maturity as measured in micronaire values ranging from about 2.0 (very fine) to 6.0 (very course). Micronaire values of about 3.8 to 4.6 are mid-range or average fineness.

As used herein, short fibre index is related to the uniformity of fibre length, as measured on the HVI. Values below 4.8 or even 4.5 are preferred.

As used herein, fibre elongation is a measure of how much the fibre stretches before it breaks, as measured on the HVI.

As used herein, the "*Fusarium* seed cotton yield" (FUSscy) is the yield of seed cotton (unginned) produced per unit area from plants grown in a field in the known presence of *Fusarium*. The "seedling %" is the percentage of seedlings from the particular line which do not show stem symptoms (browning or discolouration) of *Fusarium* infection, after cutting the stem. The "adult %" is the percentage of uninfected seedlings which remain uninfected by *Fusarium* when grown to full size. The "total %" refers to the percentage of full size plants which remain uninfected. The *Fusarium* resistance ranking (frr) for a particular line is calculated as the total % for a particular line divided by the total % for the reference variety Sicot 189, expressed as a percentage. Sicot 189 is a relatively resistant variety to *Fusarium* and therefore a *Fusarium* resistance ranking of at least 100 was preferred.

As used herein, the term "parts" includes, but is not limited to, pollen, ovule, flowers, bolls, lint, linters, shoots, roots, leaves and preferably seeds of a plant.

DETAILED DESCRIPTION OF THE INVENTION

Cotton is an important and valuable field crop. Thus, a primary goal of cotton breeding is to select and develop plants that have the traits that result in superior varieties. It is estimated that 97% of the world production of cotton is generated from varieties of two species, *Gossypium hirsutum* (Upland cotton) and *G. barbadense* (Pima cotton). Upland cotton varieties are characterised by having relatively high yield potential and tolerance to adverse climatic and growth conditions. However, the lint produced from Upland cotton varieties is of relatively low to medium quality. On the other hand, Pima cotton varieties are characterised by having less yield potential than the Upland cotton varieties and by not being as adaptable to adverse climatic or growing conditions. Yet, the quality of lint produced from Pima cotton varieties is considered high to excellent. Hence it is highly desired to combine the economically advantageous traits from the two different species in a single cotton variety.

Thus, according to one aspect of this invention there is provided a plant of the cotton (*Gossypium hirsutum*) variety designated Sicala 350B, or a part, cell, tissue or organ thereof. This variety provides lint that is unusually long and strong for *G. hirsutum*, in combination with multiple insect resistance genes in the form of expression of two Bt transgenes and good agronomic performance including a relatively high level of resistance to *Fusarium* wilt disease.

In this aspect, the invention also provides seed of the cotton variety designated Sicala 350B as well as a cotton plant produced by growing this seed.

As illustrated in the Examples below, Sicala 350B has the important characteristic of producing lint having long fibre length, good strength and mid-range micronaire. Sicala 350B was generated by crossing maternal parent variety 20435 F1 and pollen parent variety Sicot 80 as described in the Examples. A comparison of Sicala 350B to the closest variety, Sicot 80B, demonstrated that Sicala 350B produced lint with the longest fibre length commercially available in Australia (except Pima varieties). Irrigated trials and seed increase fields growing Sicala 350B have consistently produced lint with fibre length scores of at least 37, often at least 38, 39 or even 40 (as 32nds of an inch, so a score of 40 corresponds to 1.25 inches) as well as good strength and mid-range micronaire. Fibre length of lint obtained from Sicala 350B was consistently at least $\frac{1}{32}^{nd}$ of an inch longer than lint for Sicot 18B, and often more than 2 or 3×32nds longer, under a variety of growth conditions. Sicala 350B also has a role in dryland production systems as it is able to produce very good lint relative to other *G. hirsutum* varieties even under adverse seasonal conditions. Data has been obtained which indicate that although Sicala 350B was lower yielding (5-15%) than Sicot 80B in water stressed environments, the fibre length was at least 2×32nds longer than Sicot 80B fibre in these environments.

Seeds of the cotton variety of this aspect of the present invention can be generated using conventional breeding and selection techniques which are well known in the art. For example, screening techniques such as molecular marker assisted selection such as, for example, restriction fragment length polymorphism (RFLP), amplified fragment length polymorphism (AFLP), simple sequence polymorphism or microsatellite selection or other genetic marker selection, can be employed in combination with recurrent selection, pedigree breeding, transformation and/or backcrossing to generate the most suitable parental lines used for hybrid seed production.

The goal of backcrossing is to alter or substitute a single trait or characteristic in a recurrent parental line. To accomplish this, a single gene of the recurrent parental line is substituted or supplemented with the desire gene from the non-recurrent line, while retaining essentially all of the rest of the desired genes, and therefore the desired physiological and morphological constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Seeds of the cotton variety Sicala 350B were generated using a breeding process which began with the parental lines DP50BGII, 96456i and Sicot 80 as a recurrent parent as described herein and as illustrated in the Examples which follow. Once established, Sicala 350B can be propagated from hybrid seed or alternatively by using tissue culturing techniques, as described herein.

Generally, the nomenclature used herein and the laboratory procedures utilised in the present invention include well known plant breeding and selection techniques. Such techniques are thoroughly explained in the literature. See, for example, Janick, J. (2001) Plant Breeding Reviews, John Wiley & Sons, 252 p.; Jensen, N. F. ed. (1988) Plant Breeding Methodology, John Wiley & Sons, 676 p.; Richard, A. J. ed. (1990) Plant Breeding Systems, Unwin Hyman, 529 p.; Walter, F. R. ed. (1987) Plant Breeding, Vol. I Theory and Techniques, MacMillan Pub. Co.; Slavko, B. ed. (1990) Principles and Methods of Plant Breeding, Elsevier, 386 p.; and Allard, R. W. ed. (1999) Principles of Plant Breeding, John-Wiley & Sons, 240 p. Cotton breeding techniques are described by Anon. (1977). Commercial Cotton Hybrids. The ICAC Recorder. Vol. XV no. 2: 3-14; and Davis D. D. (1978) Hybrid Cotton: Specific Problems and Potentials. Adv. Agron. 30: 129-1571; all of which are incorporated by reference as if fully set forth herein. Other general references are provided throughout this document. The procedures therein are believed to be well known in the art and are provided for the convenience of the reader. All the information contained therein is incorporated herein by reference.

As illustrated in the Examples below, Sicala 350B also had the important characteristic of relatively high resistance to *Fusarium* wilt infection. Although its resistance was not complete in that a percentage of plants became infected when grown in a field known to contain *Fusarium*, the degree of resistance as expressed as a *Fusarium* resistance ranking for Sicala 350B was greater than 150. The *Fusarium* resistance ranking (frr) for a particular line was calculated as the total % for a particular line divided by the total % for the reference variety Sicot 189, expressed as a percentage.

In another aspect, the present invention provides a tissue culture of regenerable cells of the cotton variety Sicala 350B, as well as a cotton plant regenerated from the tissue culture. As used herein the phrase "tissue culture" refers to plant cells or plant parts maintained in vitro from which cotton plants can be generated, including plant protoplasts, plant calli, plant tissue clumps. Furthermore, the present invention provides plant cells that are intact in plants, or parts of plants, such as seeds, leaves, stems, pollens cells, roots, root tips, anthers, ovules, petals, flowers, embryos, fibres and bolls, from which tissue cultures can be established.

Techniques of generating plant tissue culture and regenerating plants from tissue culture are well known in the art. For example, such techniques are set forth by Vasil (1984) Cell Culture and Somatic Cell Genetics of Plants, Vol I, II, III Laboratory Procedures and Their Applications, Academic Press, New York; Green et al. (1987) Plant Tissue and Cell Culture, Academic Press, New York; Weissbach and Weissbach (1989) Methods for Plant Molecular Biology, Academic Press; Gelvin et al. (1990) Plant Molecular Biology Manual, Kluwer Academic Publishers; Evans et al. (1983) Handbook of Plant Cell Culture, MacMillian Publishing Company, New York; and Klee et al. (1987) Ann. Rev. of Plant Phys. 38:467-486. The tissue culture can be generated from cells or protoplasts of a tissue selected from the group consisting of seeds, leaves, stems, pollens, roots, root tips, anthers, ovules, petals, flowers, embryos, fibres and bolls. Techniques of generating cotton plant tissue culture and regenerating cotton plants from tissue culture are described, for example, by Umbeck et al. (1987) Bio/Technology 5:263-266; Firoozabady et al. (1987) Plant Mol. Biol. 10:105-116; Finer J. (1988) Plant Cell Rep. 6:231-234; and U.S. Pat. Nos. 5,986,181; 5,846,797.

The present invention also provides a method for producing a hybrid cotton seed, which may be an F1 hybrid seed, which comprises crossing a plant of cotton variety Sicala 350B with a different cotton plant, and harvesting the resultant cotton seed. In this aspect, the invention also extends to hybrid cotton seed produced by this method, a hybrid cotton plant produced by growing such hybrid cotton seed or a part, cell, tissue or organ of such a hybrid cotton plant, and to seed produced by growing this hybrid cotton plant. As described herein, breeding and selection techniques for production of such F1 hybrid cotton plants and seed are well known in the art.

In yet another aspect, the present invention provides a method of producing a transgenic cotton plant which comprises transforming a plant of the cotton variety Sicala 350B, or a part, cell, tissue or organ thereof, with a nucleic acid molecule comprising a foreign or non-endogenous nucleotide sequence, or an additional or modified endogenous nucleotide sequence. The nucleotide sequences used in such transformation methods are often referred to by the term "transgene". The nucleic acid molecule comprising such a transgene is preferably a gene construct which comprises the transgene and one or more expression control sequences. Preferred transgenes are those encoding a herbicide tolerance gene such as the RoundUp Ready gene or genes for modifying oil quality such as those described in WO2004072235 and WO2001079499, both hereby incorporated by reference.

In this aspect, the present invention also includes a transgenic cotton plant produced by the method described above or a part, cell, tissue or organ thereof. The invention also includes a seed of the transgenic cotton plant as well as a progeny plant produced by growing this seed, or a part, cell, tissue or organ of such a progeny plant, comprising the transgene.

Transgenes can be introduced into the plant using any of a variety of established transformation methods well-known to person skilled in the art, such as: Gressel (1985) Biotechnologically Conferring Herbicide Resistance in Crops: The Present Realities, In Molecular Form and Function of the Plant Genome, L van Vloten-Doting, (ed.), Plenum Press, New York; Huftner, S. L., et al. (1992) Revising Oversight of Genetically Modified Plants. Bio/Technology; Klee, H., et al. (1989) Plant Gene Vectors and Genetic Transformation: Plant Transformation Systems Based on the use of *Agrobacterium tumefaciens*, Cell Culture and Somatic Cell Genetics of Plants; and Koncz, C., et al (1986) Molecular and General Genetics. Techniques for transforming cotton plants are described in Umbeck et al. (1987) Bio/Technology 5:263-266; Firoozabady et al. (1987) Plant Mol.

Biol. 10:105-116; Finer and McMullen (1990) Plant Cell Rep. 8:586-589; Bayley et al. (1992) Theo. Appl. Genet. 83:45-649; Perlak et al. (1990) Bio/Technology 8:939-943; and U.S. Pat. Nos. 5,986,181; 5,846,797.

Suitable gene constructs and methods for transformation of cotton plants, parts, cells, tissues or organs and for the production of transgenic cotton plants are described by way of example in International Patent Application No. WO 01/79499 (PCT Application No. PCT/AU01/00436) in the name of Commonwealth Scientific and Industrial Research Organisation), the contents of which are incorporated herein by reference.

Transgenes may also be introduced into Sicala 350B plants by crossing these plants with a suitable cotton variety which already contains a desired transgene, optionally followed by one or more backcrosses to Sicala 350B with selection of the desired combination of characteristics.

Control of insect pests during growing of Sicala 350B, its progeny or hybrids produced therefrom is aided by the presence of transgenes encoding the Cry1Ac and Cry2Ab proteins. The genes encoding the proteins, derived from *Bacillus thuringiensis* (Bt) encode proteins that are toxic to Lepidopteran pests of cotton. The proteins, the genes encoding these and the specific transgenic events present in Sicala 350B are disclosed in U.S. patent applications published as U.S. 20040045054 (transgenic event No. 531) and U.S. 20040250317 (transgenic event 15985), both hereby incorporated by reference. The presence of the genes in the plants or plant material may be determined by detection of the genes by PCR or other methods, well known in the art, or by ELISA assays as described in Example 1 below or in the U.S. applications U.S. 20040045054 or U.S. 20040250317.

Deposit Information

A deposit of seed of cotton variety Sicala 350B is maintained at the CSIRO seed store, Australian Cotton Research Institute, Narrabri, New South Wales, Australia, and access to deposited seed will be available during the pendency of this application to persons determined by the Commissioner of Patents to be entitled thereto. Seed of the cotton variety Sicala 350B will also be made available through deposit with American Type Culture Collection, of Manassas, Virginia 20108, United States of America, under ATCC Accession No. PTA-7301.

Reference is now made to the following Examples which further illustrate the present invention in a non-limiting way.

EXAMPLES

Example 1

Materials and Methods
ELISA Assay to Detect Cry1Ac or Cry2Ab Gene Expression.

Expression of the Cry2Ab protein in cotton plants was detected by ELISA assays using an antibody raised against Cry2Aa but which also reacts with Cry2Ab protein, as follows. The ELISA assay for Cry1Ac protein was performed in an analogous manner using an antibody raised against Cry1Ab which also reacts with Cry1Ac protein. ELISA coating buffer contained, per litre, sodium carbonate ($Na_2CO_3$), 1.59 g; sodium hydrogen carbonate ($NaHCO_3$), 2.93 g; sodium chloride (NaCl), 8.77 g; made up to 1000 ml with distilled water. 10×PBST contained, per 5000 ml: sodium chloride (NaCl), 400 g; sodium hydrogen phosphate ($Na_2HPO_4 12H_2O$), 145 g; potassium dihydrogen phosphate ($KH_2PO_4$), 10 g; potassium chloride (KCl), 10 g; 35 ml of Tween 20; made up to 5000 ml with distilled water. 1×PBST was a 1/10 dilution with distilled water. ELISA substrate buffer contained, per litre, diethanolamine, 97 ml; distilled water, 800 ml; sodium azide, 0.2 g. The pH was adjusted to 9.8 with concentrated hydrochloric acid (HCl) made up to 1000 ml with distilled water and stored at 4° C. in the dark in an airtight container. ELISA extraction buffer contained per litre: NaCl, 8 g; $KH_2PO_4$, 3 g; $Na_2HPO_4 12H_2O$, 29 g; KCl, 2 g; sodium azide, 0.2 g; PVP-40, 20 g; Tween 20 (SG 1.10), 0.5 ml; made up to 1000 ml with distilled water. The solution was adjusted to pH 7.4.

On day one of the ELISA procedure, ELISA plates (Maxisorp, Nunc, Rochester N.Y. or similar) were coated with an ammonium sulphate precipitated Cry2A specific rabbit IgG fraction (at 1 μg/ml) in ELISA coating buffer (200 μl per well) and allowed to bind overnight at 4° C. The next day, the plates were washed twice with PBST, rotating the plates after the first wash so as to get a thorough washing. These plates were used immediately or stored in snap-lock bags at −20° C. Seeds were sectioned on day one, clipping one end off the seed (approximately ⅓ seed) using dog nail clippers and keeping the pointy end. The seeds were imbibed on very wet cottonwool using distilled water at room temperature overnight. On day two, the embryo was squeezed out of the seed into 96 well racked collection tubes (ThermoTrace) each containing a 3 mm chrome steel ball bearing, one embryo per tube. To each tube, 400 μl of Extraction Buffer was added, the tubes capped firmly and mixed in a Mixer Mill (Qiagen) at 30 shakes/per second for 2 minutes to disrupt the tissues. The racks of tubes were rotated and shaken a further 2 minutes. Sediment was allowed to settle for five minutes and then the caps removed.

Coated ELISA plates were prepared by adding 180 μl 1×PBST+0.2% chicken ovalbumin and Cry2A specific rabbit IgG conjugated to alkaline phosphatase using glutaraldehyde @ 1/2000 dilution per well. 20 μl of ground seed sample was added per well using wide bore tips (ThermoTrace). The plates were covered and left overnight at 4° C. in a moist, sealed box to prevent drying out of the samples. On day three, samples were decanted and the wells washed twice with PBST, rotating the plates each wash to ensure thorough washing. 150 μl of Substrate Buffer containing Sigma 104 Phosphatase Substrate (nitrophenylphosphate) (56 mg/100 ml) was added to each well. Plates were left at room temperature for 1 to 2 hours for colour to develop. Positive samples (ie seed extracts containing Cry2A protein) gave a bright yellow colour. Negative samples stayed clear. The colour reaction could be stopped by adding 30 μL 0.3M sodium hydroxide per well.

Plant Characteristics

The leaf hair phenotype of plants was assessed visually and given a score from 0 (glabrous) to 4 (hairy). Scores of <4 were preferred. Resistance was assessed to the disease bacterial blight of cotton, caused by *Xanthomonas axonopodis*. Plants were selected that were free of water soaked lesions two weeks or more after a spray with a suspension of *X. axonopodis* cells, race 18.

Resistance was also assessed to *Fusarium* and *Verticillium* wilts, caused by the fungi *Fusarium oxysporum* f. sp. *vasinfectum* and *Verticillium dahliae*, respectively, by growing the plants in the soil known to contain the organisms. The *Fusarium* fungus affected susceptible cotton seedlings or more often more mature plants. Affected plants were first darker green and stunted, followed by yellowing of the leaves and dying or loss of foliage.

Symptoms typically first appeared on lower leaves around the time of first flower. The leaf margins then wilted, turning yellow and then brown. Infected plants fruited earlier than normal with smaller bolls that opened prematurely. A diagonal cut across the stem typically revealed vascular discoloration just beneath the bark extending down the tap root. Wilting occurred rapidly following rain preceded by a dry spell. *Verticillium* wilt fungus was also known to infect the roots and grow in the xylem, blocking water uptake and thereby causing wilt symptoms. Affected seedlings typically yellowed, dried out and died. Larger plants were stunted and leaves showed a yellowing of the margin and the areas between the main veins. These areas eventually died leaving leaves with a scorched appearance. Symptoms typically first appear on the lower leaves. A dark-brown discolouration of the water-conducting tissues of the roots and stem was also evident in susceptible plants. Severely affected plants tended to shed leaves and bolls. Resistance to *Fusarium* and *Verticillium* was scored relative to known resistant cultivars, in particular Sicot 189.

Fibre Quality and Yield

Lint (seed-free) was obtained from harvested (seed) cotton by ginning on a 20 saw gin and weighed. Lint % (gin turnout) was expressed as the weight of the lint as a percentage of the weight of the seed cotton. Values between 40 and 44 were preferred. Yield (Yld) of lint was expressed as kg/ha. Fibre quality was measured on duplicate samples using an Uster HVI900SA. Measurements were made of fibre length (len), fibre strength (str), uniformity (uni), short fibre index (sfi), elongation (el), micronaire (mic), maturity (mr), maturity percentage (mp), fineness (fin) and neps per gram. Long and strong fibres with intermediate micronaire (3.8 to 4.5) were preferred.

Example 2

In 1998, seed of *G. hirsutum* line CPI140533, which was DP50BGII containing both the Cry1Ac and Cry2Ab genes, was imported from Monsanto Corp. USA by Monsanto Australia. Some seed of this line was provided to CSIRO Plant Industry by Dr Stewart Addison and crossed initially with a *G. hirsutum* breeding line designated 96456i (maintained at the CSIRO seed store, ACRI, Narrabri, New South Wales, Australia) which also contained the Cry1Ac gene. F1 progeny were crossed with *G. hirsutum* cv. Sicot 80 (Australian Plant Breeders Rights Application No. 2001/165) in a PC2 glasshouse at the Australian Cotton Research Institute (ACRI), Narrabri, New South Wales, Australia. In these crosses, F1 progeny were selected on the basis of Cry1Ac and Cry2Ab expression, plant habit and morphology including smooth leaf. Progeny that contained the Cry1Ac and Cry2Ab genes were used in three subsequent backcross generations with Sicot 80 as the recurrent parent using Sicot 80 as the pollen donor, each time selecting for maintenance of Cry1Ac and Cry2Ab gene expression as described in Example 1, with the final cross being line $20435F_1$×Sicot 80. Following a selfing generation in the glasshouse in winter of 2001, approximately 400 individual seed were sown in the field in the Spring of 2001 and approximately 80 plants selected on the basis of Cry1Ac and Cry2Ab expression, assayed by ELISA on leaf protein extracts. These plants were assessed for leaf hair and disease resistance, and on maturity for lint %, fibre quality including fibre length, strength, uniformity and micronaire, and gin turnout.

The data for 38 of the plants and the recurrent parent Sicot 80B are shown in Table 1. It was noted that one particular plant, No. 21 in Table 1, provided lint that was unusually and unexpectedly long and strong, significantly longer and stronger than for Sicot 80B. Furthermore, this combination of length and strength was not seen for the initial parent DP50B either.

TABLE 1

Comparison of 38 BC4F2 plants in the field, 2001/02

| line | gin | len | uni | sfi | str | el | mic |
|---|---|---|---|---|---|---|---|
| 1 | 42.2 | 1.18 | 84.3 | 5.5 | 31.6 | 13.2 | 4.9 |
| 4 | 43.1 | 1.15 | 85.7 | 4.6 | 31.4 | 14.3 | 4.6 |

TABLE 1-continued Comparison of 38 BC4F2 plants in the field, 2001/02

| line | gin | len | uni | sfi | str | el | mic |
|---|---|---|---|---|---|---|---|
| 5 | 40.7 | 1.21 | 85.5 | 4.8 | 33.3 | 12.1 | 4.6 |
| 11 | 44.7 | 1.16 | 84.3 | 6.0 | 31.6 | 14.3 | 4.9 |
| 14 | 43.6 | 1.17 | 84.9 | 5.8 | 31.5 | 11.6 | 4.6 |
| 15 | 44.2 | 1.19 | 84.9 | 5.3 | 31.8 | 12.4 | 4.8 |
| 18 | 42.7 | 1.17 | 85.7 | 4.7 | 31.5 | 11.9 | 4.6 |
| 19 | 43.4 | 1.19 | 84.7 | 5.8 | 30.6 | 13.5 | 4.9 |
| 21 | 40.5 | 1.28 | 85.4 | 4.2 | 34.6 | 9.7 | 4.3 |
| 25 | 43.7 | 1.19 | 85.4 | 4.3 | 32.8 | 13.0 | 4.4 |
| 26 | 43.9 | 1.16 | 86.5 | 4.4 | 32.2 | 11.4 | 4.9 |
| 27 | 43.0 | 1.16 | 84.8 | 6.7 | 32.3 | 11.6 | 4.8 |
| 31 | 43.5 | 1.19 | 85.7 | 5.0 | 30.8 | 12.2 | 4.7 |
| 32 | 40.5 | 1.24 | 86.0 | 3.7 | 33.2 | 11.7 | 4.6 |
| 33 | 42.3 | 1.19 | 85.1 | 5.1 | 32.3 | 10.2 | 4.8 |
| 34 | 40.8 | 1.20 | 86.2 | 4.0 | 35.6 | 13.6 | 4.9 |
| 36 | 43.1 | 1.17 | 84.9 | 6.2 | 32.8 | 12.0 | 4.9 |
| 38 | 42.7 | 1.25 | 85.7 | 3.8 | 36.1 | 11.8 | 4.9 |
| 40 | 43.4 | 1.20 | 85.6 | 4.7 | 33.5 | 12.1 | 4.8 |
| 41 | 44.3 | 1.18 | 85.4 | 4.5 | 31.8 | 12.9 | 4.6 |
| 48 | 39.6 | 1.24 | 85.1 | 4.8 | 33.9 | 11.3 | 4.6 |
| 49 | 40.3 | 1.19 | 85.2 | 4.7 | 31.0 | 10.8 | 4.6 |
| 56 | 43.5 | 1.20 | 85.4 | 5.6 | 32.3 | 11.1 | 4.8 |
| 58 | 42.0 | 1.23 | 87.0 | 4.4 | 32.7 | 11.8 | 4.9 |
| 59 | 42.7 | 1.12 | 85.0 | 5.4 | 31.1 | 13.7 | 4.9 |
| 61 | 43.4 | 1.14 | 83.3 | 9.4 | 30.5 | 13.2 | 4.7 |
| 65 | 41.9 | 1.17 | 84.7 | 5.4 | 33.5 | 12.4 | 4.9 |
| 66 | 41.9 | 1.19 | 84.8 | 5.5 | 33.1 | 12.5 | 4.7 |
| 68 | 41.9 | 1.17 | 82.3 | 7.4 | 33.5 | 10.6 | 4.3 |
| 71 | 42.1 | 1.22 | 86.4 | 4.2 | 33.5 | 10.8 | 4.9 |
| 73 | 43.1 | 1.16 | 86.8 | 3.9 | 31.6 | 12.4 | 4.8 |
| 74 | 43.7 | 1.20 | 84.5 | 5.5 | 31.1 | 12.1 | 4.8 |
| 79 | 41.3 | 1.25 | 85.0 | 4.5 | 33.4 | 10.4 | 4.2 |
| 82 | 42.9 | 1.17 | 85.6 | 4.6 | 31.0 | 12.2 | 4.8 |
| 83 | 41.3 | 1.19 | 86.4 | 4.5 | 32.0 | 11.3 | 4.8 |
| 87 | 41.8 | 1.18 | 85.4 | 5.5 | 32.8 | 14.1 | 4.7 |
| 88 | 44.6 | 1.10 | 85.2 | 6.6 | 30.7 | 12.3 | 4.9 |
| 89 | 40.0 | 1.17 | 85.1 | 5.4 | 32.5 | 11.2 | 4.6 |
| Sicot 80B | 43.4 | 1.20 | 84.9 | 5.1 | 32.8 | 12.1 | 4.9 |

Progeny plants from the 38 plants, after selfing, were grown in the field in the following season (2002/03) as progeny rows, each row corresponding to an individual line. These were designated the 20461 series of lines. Progeny rows were assessed for yield, disease resistance and fibre quality. Line 21 was once again the outstanding line, providing the maximum fibre quality in terms of both length and strength amongst the 38 lines. Line 21 also easily out-performed the control varieties (Table 2). However, the yield of line 21 was reduced compared to other lines.

Thirteen of the lines proceeded to replicated, multi site trials in 2003/04 and 2004/05. The data are presented in Table 3. The fibre quality of Line 21, now designated Sicala 350B, was maintained in the trials at all of the sites. Fibre length for Sicala 350B under well-watered (irrigated) conditions was at least 1.25 inches and strength was at least 31.7 g/tex at each site. Fiber uniformity for the tested lines as measured by the HVI was the greatest for Sicala 350B, greater than 85. Yield for Sicala 350B was reduced compared to its recurrent parent Sicot 80B by an average of 17% (Table 3). However, the premium prices that fibre of such quality usually attract would be expected to compensate for the reduced yield.

Over the seasons of trialing to date, emphasis was placed on yield and fibre quality and resistance to insect pests and *Verticillium* and *Fusarium* wilts, which were all high. In particular, Sicala 350B expressed the Cry1Ac and Cry2Ab proteins due to the presence of transgenes encoding these "Bt proteins". Other characteristics of Sicala 350B: it was a vigorous full season plant type, adapted to full season and dryland conditions, having good disease resistance including a *Fusarium* resistance rank of 117, and normal seed size (9320 seeds/kg). Sicala 350B was found to be uniform and stable in these characteristics for at least 5 generations.

TABLE 2

Yield, disease resistance and fibre quality data for progeny row testing in the field, 2002/03.

| Line | GIN | LEN | UNI | SFI | STR | EL | MIC | Yld | FUSscy | seedling % | adult % | total % | frr |
|---|---|---|---|---|---|---|---|---|---|---|---|---|---|
| 20461-1 | 42.6 | 1.18 | 84.3 | 7.4 | 29.6 | 8.2 | 4.8 | 2956 | 4369 | 74 | 82 | 61 | 144 |
| 20461-4 | 43.2 | 1.18 | 83.1 | 8.2 | 28.2 | 8.3 | 4.5 | 3000 | 3538 | 94 | 64 | 59 | 139 |
| 20461-5 | 41.8 | 1.22 | 83.4 | 7.9 | 29.0 | 7.1 | 4.3 | 2834 | 3826 | 79 | 52 | 42 | 98 |
| 20461-11 | 43.6 | 1.17 | 84.7 | 7.1 | 29.4 | 8.7 | 5.0 | 2888 | 4069 | 80 | 64 | 52 | 123 |
| 20461-14 | 42.5 | 1.20 | 82.9 | 8.6 | 28.1 | 7.2 | 4.6 | 2701 | 4392 | 79 | 83 | 65 | 153 |
| 20461-15 | 44.3 | 1.17 | 83.7 | 7.9 | 29.4 | 7.8 | 5.0 | 2931 | 4109 | 87 | 81 | 70 | 164 |
| 20461-18 | 43.2 | 1.15 | 83.0 | 8.0 | 29.0 | 7.7 | 4.5 | 2824 | 4028 | 78 | 67 | 52 | 123 |
| 20461-19 | 43.0 | 1.16 | 83.4 | 7.9 | 29.3 | 7.8 | 4.5 | 2936 | 3870 | 75 | 57 | 44 | 103 |
| 20461-21 | 39.9 | 1.30 | 85.3 | 6.7 | 31.7 | 6.3 | 4.5 | 2810 | 4448 | 82 | 82 | 68 | 158 |
| 20461-25 | 44.2 | 1.18 | 83.4 | 8.5 | 28.8 | 8.3 | 4.5 | 2998 | 4232 | 83 | 72 | 60 | 140 |
| 20461-26 | 42.8 | 1.15 | 83.1 | 8.3 | 30.1 | 7.6 | 4.8 | 2881 | 3974 | 86 | 81 | 69 | 162 |
| 20461-27 | 41.3 | 1.16 | 83.6 | 8.2 | 31.1 | 7.2 | 5.1 | 2707 | 3976 | 86 | 78 | 67 | 156 |
| 20461-31 | 42.2 | 1.14 | 82.1 | 9.0 | 28.0 | 8.5 | 4.8 | 2921 | 4114 | 83 | 71 | 60 | 140 |
| 20461-32 | 40.3 | 1.19 | 83.8 | 8.0 | 30.4 | 7.0 | 5.0 | 2775 | 4058 | 83 | 87 | 71 | 167 |
| 20461-33 | 41.2 | 1.22 | 83.8 | 7.6 | 29.6 | 6.7 | 4.7 | 2996 | 4376 | 83 | 83 | 69 | 161 |
| 20461-34 | 41.7 | 1.21 | 84.0 | 7.3 | 30.6 | 7.8 | 5.0 | 2892 | 4158 | 74 | 71 | 56 | 131 |
| 20461-36 | 43.9 | 1.14 | 83.4 | 8.5 | 29.0 | 7.7 | 5.0 | 2815 | 4189 | 82 | 72 | 60 | 141 |
| 20461-38 | 40.6 | 1.24 | 84.3 | 7.6 | 32.3 | 6.8 | 5.0 | 3016 | 3923 | 81 | 75 | 62 | 145 |
| 20461-40 | 42.9 | 1.15 | 82.8 | 8.3 | 29.3 | 8.0 | 5.0 | 2804 | 3914 | 82 | 73 | 61 | 142 |
| 20461-41 | 42.1 | 1.20 | 84.1 | 7.4 | 28.8 | 7.1 | 4.9 | 2921 | 3833 | 80 | 74 | 60 | 140 |
| 20461-48 | 42.5 | 1.20 | 83.8 | 7.7 | 29.3 | 7.4 | 4.9 | 3061 | 4005 | 76 | 66 | 49 | 115 |
| 20461-49 | 40.0 | 1.18 | 83.7 | 7.7 | 30.8 | 7.3 | 4.6 | 2579 | 3759 | 78 | 81 | 63 | 147 |
| 20461-56 | 42.8 | 1.19 | 83.9 | 8.1 | 29.2 | 7.4 | 4.7 | 3080 | 4199 | 80 | 60 | 48 | 114 |
| 20461-58 | 41.6 | 1.22 | 83.6 | 8.1 | 31.0 | 6.9 | 4.9 | 2872 | 4321 | 76 | 66 | 52 | 122 |
| 20461-59 | 43.3 | 1.19 | 83.4 | 8.2 | 28.8 | 7.7 | 4.9 | 2754 | 4119 | 82 | 74 | 60 | 141 |
| 20461-61 | 42.4 | 1.15 | 82.1 | 9.3 | 28.4 | 7.4 | 5.0 | 2873 | 4074 | 83 | 77 | 63 | 149 |
| 20461-65 | 42.3 | 1.17 | 83.1 | 8.5 | 30.5 | 7.3 | 4.9 | 2917 | 4097 | 81 | 65 | 52 | 123 |
| 20461-66 | 40.9 | 1.16 | 82.4 | 9.1 | 30.6 | 7.1 | 5.1 | 2841 | 4279 | 75 | 66 | 50 | 118 |
| 20461-68 | 42.2 | 1.17 | 82.6 | 9.1 | 28.4 | 7.2 | 4.8 | 2868 | 3891 | 78 | 71 | 55 | 128 |

TABLE 2-continued

Yield, disease resistance and fibre quality data for progeny row testing in the field, 2002/03.

| Line | GIN | LEN | UNI | SFI | STR | EL | MIC | Yld | FUSscy | seedling % | adult % | total % | frr |
|---|---|---|---|---|---|---|---|---|---|---|---|---|---|
| 20461-71 | 42.0 | 1.23 | 84.2 | 7.4 | 30.6 | 7.2 | 4.8 | 2692 | 4048 | 73 | 72 | 53 | 123 |
| 20461-73 | 42.3 | 1.18 | 83.4 | 8.2 | 30.3 | 7.4 | 4.8 | 2863 | 4419 | 89 | 91 | 80 | 188 |
| 20461-74 | 42.2 | 1.18 | 83.9 | 7.6 | 28.4 | 7.3 | 4.9 | 3057 | 4764 | 80 | 63 | 51 | 119 |
| 20461-79 | 41.7 | 1.24 | 83.7 | 8.1 | 29.9 | 7.0 | 4.7 | 2813 | 3892 | 78 | 65 | 51 | 119 |
| 20461-82 | 42.6 | 1.16 | 82.6 | 8.2 | 28.9 | 7.6 | 4.6 | 3036 | 4211 | 74 | 59 | 44 | 104 |
| 20461-83 | 42.5 | 1.19 | 83.5 | 8.3 | 28.7 | 7.1 | 4.5 | 2659 | 3891 | 71 | 62 | 43 | 100 |
| 20461-87 | 42.2 | 1.15 | 83.9 | 7.3 | 29.5 | 9.1 | 4.7 | 2847 | 3719 | 84 | 61 | 51 | 120 |
| 20461-88 | 44.8 | 1.13 | 82.8 | 8.5 | 28.0 | 7.9 | 5.2 | 2959 | 3797 | 74 | 71 | 52 | 122 |
| 20461-89 | 41.0 | 1.18 | 83.2 | 8.0 | 29.4 | 7.4 | 4.6 | 2804 | 3870 | 85 | 72 | 61 | 143 |
| Sicot 289i | 43.4 | 1.18 | 83.1 | 8.1 | 29.4 | 6.4 | 5.0 | 3171 | 4199 | 81 | 50 | 40 | 95 |
| Sicala V-3i | 42.6 | 1.13 | 83.2 | 8.2 | 30.1 | 6.2 | 4.8 | 3384 | 4009 | 69 | 58 | 41 | 95 |
| 20416-2 | 42.3 | 1.19 | 84.0 | 7.6 | 28.3 | 7.6 | 4.9 | 2995 | 3829 | 81 | 62 | 54 | 127 |
| Sicot 189 | 42.6 | 1.17 | 83.2 | 8.6 | 31.5 | 7.0 | 4.8 | 3053 | 3621 | 68 | 60 | 43 | 100 |
| Sicot 80B | 41.9 | 1.20 | 84.1 | 7.5 | 29.9 | 7.4 | 4.9 | 2989 | 4283 | 81 | 71 | 58 | 137 |

GIN = gin turnout;
LEN = length of lint as measured by HVI;
UNI = uniformity index;
SFI = short fibre index;
STR = strength;
EL = elongation index;
MIC = micronaire;
Yld = yield of ginned lint (kg/ha);
FUSscy = Fusarium seed cotton yield (kg/ha);
frr = Fusarium resistance ranking relative to Sicot 189.

TABLE 3

Data from replicated multi-site trials for growth of Sicala 350B.

| line | Mv1 | Mv2 | sg | em | mo | bb | mean | gin | len | uni | sfi | str | el | mic | mr | mp | fin | Fscy | FRR | neps |
|---|---|---|---|---|---|---|---|---|---|---|---|---|---|---|---|---|---|---|---|---|
| 20461-11 | 2888 | 1920 | 2678 | 2000 | 1838 | 1961 | 2079 | 39.6 | 1.18 | 83.7 | 9.1 | 29.0 | 8.2 | 4.5 | 0.87 | 77.4 | 193 | 1890 | 97 | 111 |
| 20461-1 | 2956 | 1848 | 2666 | 2022 | 1638 | 1989 | 2033 | 39.1 | 1.21 | 84.0 | 8.8 | 28.9 | 7.5 | 4.4 | 0.88 | 78.3 | 190 | 2028 | 93 | 105 |
| 20461-74 | 3057 | 1908 | 2453 | 2001 | 1663 | 1996 | 2004 | 38.9 | 1.22 | 83.8 | 8.9 | 29.6 | 6.9 | 4.4 | 0.88 | 78.5 | 187 | 2467 | 110 | 114 |
| 20461-33 | 2996 | 1898 | 2511 | 2057 | 1625 | 1842 | 1987 | 38.8 | 1.21 | 83.6 | 8.8 | 28.5 | 6.7 | 4.3 | 0.89 | 79.1 | 181 | 2608 | 116 | 125 |
| 20461-38 | 3016 | 1826 | 2484 | 2014 | 1666 | 1874 | 1973 | 38.0 | 1.23 | 84.2 | 8.4 | 31.3 | 6.8 | 4.5 | 0.88 | 78.7 | 190 | 2858 | 127 | 99 |
| 20461-34 | 2892 | 1827 | 2557 | 1909 | 1619 | 1938 | 1970 | 38.7 | 1.20 | 84.2 | 8.5 | 30.7 | 7.7 | 4.5 | 0.89 | 79.5 | 190 | 2084 | 93 | 96 |
| 20461-65 | 2917 | 1804 | 2557 | 1901 | 1546 | 1851 | 1932 | 38.5 | 1.19 | 83.0 | 9.4 | 30.2 | 7.0 | 4.4 | 0.89 | 79.2 | 186 | 1869 | 96 | 130 |
| 20461-15 | 2931 | 1834 | 2594 | 1953 | 1548 | 1917 | 1969 | 39.3 | 1.19 | 83.0 | 9.4 | 29.1 | 7.3 | 4.4 | 0.85 | 76.3 | 187 | 1679 | 86 | 138 |
| 20461-73 | 2863 | 1809 | 2476 | 1998 | 1557 | 1915 | 1951 | 37.9 | 1.18 | 83.1 | 9.4 | 28.8 | 7.1 | 4.4 | 0.88 | 78.8 | 187 | 1989 | 92 | 126 |
| 20461-56 | 3080 | 1767 | 2526 | 1949 | 1565 | 1877 | 1937 | 39.3 | 1.20 | 83.0 | 9.2 | 28.5 | 7.1 | 4.3 | 0.87 | 77.6 | 185 | 1888 | 78 | 135 |
| 20461-82 | 3036 | 1809 | 2468 | 2040 | 1493 | 1844 | 1931 | 39.1 | 1.18 | 83.2 | 9.5 | 28.0 | 7.4 | 4.2 | 0.86 | 76.8 | 182 | 1854 | 98 | 141 |
| 20461-68 | 2868 | 1719 | 2444 | 1909 | 1452 | 1822 | 1869 | 38.0 | 1.20 | 82.6 | 9.9 | 29.1 | 6.8 | 3.9 | 0.84 | 75.0 | 171 | 2315 | 113 | 173 |
| 20461-21 | 2810 | 1557 | 2263 | 1916 | 1302 | 1582 | 1724 | 36.8 | 1.28 | 85.1 | 8.1 | 32.0 | 6.0 | 4.2 | 0.89 | 79.6 | 175 | 1982 | 113 | 101 |
| Sicot 289i |  | 1841 | 2621 | 2125 | 1596 | 1897 | 2016 | 39.8 | 1.18 | 83.0 | 9.2 | 30.1 | 6.6 | 4.6 | 0.92 | 81.7 | 185 | 1858 | 101 | 124 |
| 20416-2 |  | 1829 | 2502 | 2022 | 1547 | 1897 | 1959 | 37.9 | 1.21 | 84.3 | 8.9 | 28.5 | 7.1 | 4.1 | 0.87 | 77.2 | 182 | 2514 | 107 | 114 |
| Sicot 80B | 2989 | 1888 | 2532 | 2018 | 1698 | 1918 | 2011 | 38.8 | 1.21 | 83.8 | 8.8 | 29.6 | 7.2 | 4.4 | 0.88 | 78.4 | 188 | 2456 | 113 | 112 |
| Sicala 350B | 2810 | 1557 | 2263 | 1916 | 1302 | 1582 | 1724 | 36.8 | 1.28 | 85.1 | 8.1 | 32.0 | 6.0 | 4.2 | 0.89 | 79.6 | 175 | 1982 | 113 | 101 |
| Y diff | 106% | 121% | 112% | 105% | 130% | 121% | 117% | | | | | | | | | | | | | |

Lint yields (kg/ha):
Mv1 = Myal Vale trial site yield in 2003/04;
Mv2 = Myal Vale trial site in 2004/05;
sg = Saint George trail site;
em = Emerald trial site;
mo = Moree trial site;
bb = Boggabilla trial site.
mr = maturity ratio (HVI);
mp = maturity percentage (HVI);
fin = fineness (millitex, HVI);
neps = neps/g.

Example 3

Sicala 350B (breeders code 20461-21; also known as CSX 21B) was produced as described in Example 2 by controlled pollination using variety 20435 F1 (breeder: Commonwealth Scientific and Industrial Research Organisation) as the maternal seed parent and Sicot 80 (Australian PBR No. 2001/165, registered 30 Jun. 2003; breeder: Commonwealth Scientific and Industrial Research Organisation) as the pollen parent.

Results of multi-site field tests of Sicala 350B and comparisons with other varieties are set 10 out in the following tables. It was also observed that Sicala 350B produced fibre of significantly greater length and strength than its parent variety Sicot 80 (or Sicot 80B) under dryland (non-irrigated) growing conditions, typically where many varieties suffer from stress-related problems, indicating its utility under a variety of growth conditions.

A. Results 2003/04 and 2004/05 (12 sites · small scale)

| | Yield (b/ha) | Length Inches (32nds) | Micronaire | Strength (grams/tex) |
|---|---|---|---|---|
| Sicot 80B | 10.5 | 1.21 (39) | 4.4 | 30.2 |
| Sicala 350B | 9.6 | 1.27 (41) | 4.1 | 31.8 |
| Sicot 71B | 11.7 | 1.20 (38) | 4.2 | 29.5 |
| Sicot 289B | 10.8 | 1.19 (38) | 4.5 | 30.1 |

B. Trial Emerald, Queensland Australia, 2003 (391 em)

| | Yield (kg/ha) | Length (Inches) | Strength (grams/tex) | Micronaire |
|---|---|---|---|---|
| Sicala 350B | 1916 | 1.26 | 32.7 | 4.2 |
| Sicot 80B | 2018 | 1.2 | 29.8 | 4.4 |
| Sicot 71B | 2280 | 1.21 | 29.0 | 4.2 |
| Sicot 289B | 2025 | 1.18 | 29.9 | 4.4 |

C. Large Scale Trial, Emerald 2005 (CT05-95)

| | Yield (b/ha) | Length Inches (32nds) | Micronaire | Strength (grams/tex) |
|---|---|---|---|---|
| Sicot 80B | 8.62 | 1.14 (37) | 4.7 | 31.0 |
| Sicala 350B | 7.81 | 1.24 (40) | 4.3 | 33.5 |
| difference | −0.81 | 0.10 (3) | −0.4 | +2.5 |

D. Large Scale Trial, Theodore, Queensland Australia, 2005 (CT05-70)

| | Yield (b/ha) | Length Inches (32nds) | Micronaire | Strength (grams/tex) |
|---|---|---|---|---|
| Sicot 80B | 9.41 | 1.15 (37) | 4.8 | 30.0 |
| Sicala 350B | 8.20 | 1.22 (39) | 4.5 | 33.0 |
| difference | −1.21 | +0.07 (2) | −0.3 | +3.0 |

E. Large Scale Trial, Narrabri, New South Wales Australia, 2005

| | Yield (b/ha) | Length Inches (32nds) | Micronaire | Strength (grams/tex) |
|---|---|---|---|---|
| Sicot 80B | 11.14 | 38 | 4.6-4.9 | 27.1-31.9 |
| Sicala 350B | 10.91 | 40 | 3.8-4.5 | 32 + above |
| difference | −0.23 | +2 | − | + |

F. Dryland data (six sites NSW and QLD, 2003/04 and 2004/05)

| | Yield (b/ha) | Length Inch | Micronaire | Strength (g/tex) |
|---|---|---|---|---|
| Sicot 80B | 3.98 | 1.12 (36) | 4.1 | 29.0 |
| Sicala 350B | 3.75 | 1.19 (38) | 4.0 | 32.1 |
| difference | −0.23 | 0.07 (=2) | −0.11 | +3.1 |

G. Dryland Trial, Condamine 2005 (CT05-18)

| | Yield (b/ha) | Length Inches (32nds) | Micronaire | Strength (grams/tex) |
|---|---|---|---|---|
| Sicot 80B | 1.86 | 1.06 (34) | 4.4 | 29.3 |
| Sicala 350B | 1.66 | 1.12 (36) | 4.2 | 31.3 |
| difference | −0.20 | +0.06 (2) | −0.2 | +0.2 |

Example 4

Production of Hybrid Seed from Sicala 350B

Plants of Sicala 350B are crossed with cotton plants of a variety that is transgenic for a gene conferring tolerance to a herbicide such as, for example, glyphosate (Roundup), such as Sicot 289BR. Preferably, the herbicide gene provides tolerance to the cotton plant throughout the growing season, allowing application of the herbicide and therefore weed control in the fields throughout the season; in the case of a glyphosate tolerance gene, such a gene may also be known as "Roundup Ready Flex". The progeny plants are backcrossed to either Sicala 350B as a recurrent parent for several generations to provide a herbicide tolerant form of Sicala 350B, or to the herbicide tolerant parent to provide a variety that provides premium fibre quality. Plants of Sicala 350B may also be crossed in a similar fashion with cotton plants having other desirable features such as additional disease resistance or certain oil characteristics such as, for example, high oleic acid, high stearic acid or low palmitic acid forms.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Unless the context indicates otherwise, the reference to any prior art in this specification is not, and should not be taken as, an acknowledgment or any form of suggestion that the prior art forms part of the common general knowledge in Australia.

The invention claimed is:

1. A plant of the cotton (*Gossypium Hirsutum*) variety Sicala 350B, or a cell, tissue or organ thereof, wherein seed of a representative plant has been deposited under ATCC No. PTA-7301.

2. A seed of the cotton (*Gossypiurn Hirsutum*) variety Sicala 350B, wherein a sample of the seed has been deposited under ATCC No. PTA-7301.

3. A process for producing a cotton plant comprising growing the seed of claim 2, thereby producing the cotton plant.

4. A tissue culture of regenerable cells of the cotton plant of claim 1.

5. The tissue culture of claim 4 wherein the tissue culture regenerates plants having all the morphological and physiological characteristics of said cotton plant.

6. The tissue culture of claim 5 wherein said tissue culture is generated from cells or protoplasts of a tissue selected from the group consisting of seeds, leaves, stems, pollens, roots, root tips, anthers, ovules, petals, flowers, embryos, and bolls.

7. A cotton plant regenerated from the tissue culture of claim 4, or a cell, tissue or organ of said cotton plant, wherein said cotton plant has all the morphological and physiological characteristics of Sicala 350B.

8. A process for producing F1 hybrid cotton seed, comprising crossing the cotton plant of claim 1 with a different cotton plant, and harvesting the resultant F1 hybrid cotton seed.

9. The process of claim 8 wherein the F1 hybrid cotton seed comprises a gene that confers herbicide tolerance to plant cells in which it is expressed.

10. A hybrid cotton seed produced by the process of claim 8, wherein one parent of the cotton seed is cotton variety Sicala 350B.

11. A hybrid cotton plant produced by growing the hybrid cotton seed of claim 10, or a cell, tissue or organ of said hybrid cotton plant wherein one parent of the hybrid cotton plant is cotton variety Sicala 350B.

12. The hybrid cotton plant of claim 11 which comprises a gene that confers herbicide tolerance to the plant.

13. A process of producing cotton seed, comprising growing the hybrid cotton plant of claim 11 and harvesting the resultant seed.

14. A seed of cotton variety Sicala 350B, wherein seed of a representative plant of the variety Sicala 350B has been deposited under ATCC No. PTA-7301.

15. A process of producing a transgenic cotton plant, comprising transforming the cotton plant of claim 1, or a cell, tissue or organ thereof, with a nucleic acid molecule comprising a foreign or non-endogenous nucleotide sequence or an additional or modified endogenous nucleotide sequence.

16. The process of claim 15, wherein said nucleic acid molecule also comprises one,or more expression control sequences.

17. A process of producing lint, comprising the steps of growing the cotton plant of claim 1 and harvesting lint from said cotton plant.

18. The process of claim 17, further comprising the step of ginning the lint so as to separate the lint from seed.

19. A process for producing a cotton plant comprising growing the seed of claim 14, thereby producing the cotton plant.

20. A process of producing lint, comprising the steps of growing the cotton plant of claim 11 and harvesting lint from said cotton plant.

21. The process of claim 20, further comprising the step of ginning the lint so as to separate the lint from seed.

* * * * *